United States Patent [19]

Yamaguchi et al.

[11] Patent Number: 4,618,714

[45] Date of Patent: Oct. 21, 1986

[54] PROCESS FOR PREPARATION OF 3,3'- OR 3,4'-DIAMINOBENZOPHENONES

[75] Inventors: Keizaburo Yamaguchi, Kanagawa; Kenichi Sugimoto, Tokyo; Yoshimitsu Tanabe, Kanagawa; Saburo Kawashima, Kanagawa; Akihiro Yamaguchi, Kanagawa, all of Japan

[73] Assignee: Mitsui Toatsu Chemicals, Inc., Tokyo, Japan

[21] Appl. No.: 490,546

[22] Filed: May 2, 1983

[30] Foreign Application Priority Data

Mar. 23, 1983 [JP] Japan ................................ 58-47097

[51] Int. Cl.[4] ............................................. C07C 97/10
[52] U.S. Cl. .................................. 564/329; 564/411; 564/412

[58] Field of Search ................ 564/325, 330, 338, 412

[56] References Cited

U.S. PATENT DOCUMENTS

| 3,213,139 | 10/1965 | Chase | 564/325 |
| 3,465,038 | 9/1969 | Dolan | 564/329 X |
| 3,541,151 | 11/1970 | Coombs et al. | 564/327 X |

*Primary Examiner*—Robert V. Hines
*Attorney, Agent, or Firm*—Jeffers, Irish & Hoffman

[57] ABSTRACT

Preparation of 3,3'- or 3,4'-diaminobenzophenone by nitrating a chloronitrobenzophenone mixture obtained by the Friedel-Crafts reaction between 3- or 4-nitrobenzoyl chloride and chlorobenzene, and catalytically reducing and dechlorinating the resulting chlorodinitrobenzophenone mixture in the presence of a reduction catalyst and a dehydrochlorinating agent.

5 Claims, No Drawings

PROCESS FOR PREPARATION OF 3,3'- OR 3,4'-DIAMINOBENZOPHENONES

BACKGROUND OF THE INVENTION

The present invention relates to a novel process for the preparation of 3,3'- or 3,4'-diaminobenzophenone.

3,3'-Diaminobenzophenone and 3,4'-diaminobenzophenone are useful as monomers for the production of heat-resistant high-molecular compounds, intermediates for the production of agricultural chemicals, pharmacological compounds and dyes, particularly as starting materials for the production of polyamides and polyimides.

Heretofore, these diaminobenzophenones have been prepared by reducing the corresponding dinitrobenzophenones. For example, 3,3'-diaminobenzophenone has been prepared by reducing 3,3'-dinitrobenzophenone in the presence of a tin compound in a large amount of concentrated hydrochloric acid [L.H. Kloron et al., J. Org. Chem., 23, 351(1958)]. 3,4'-Diaminobenzophenone has been prepared by reducing 3,4'-dinitrobenzophenone in the presence of a tin compound [I. Moyer. Hunsberger et al., J. Am. Chem. Soc., 71, 2637(1949)].

However, it is very difficult to industrialize these processes, because there has been no method of advantageously preparing 3,3'- or 3,4'-dinitrobenzophenone as the starting material. For example, 3,3'-dinitrobenzophenone may be prepared by nitrating benzophenone, but the resulting product is composed of a mixture containing various isomers or the like. In order to isolate the desired 3,3'-dinitro compound, large amounts of solvents must be used and purification by recrystallization must be repeated [E. Barmatt et al., J. Chem. Soc., 125, 767(1924)]. For this reason, the yield of 3,3'-dinitrobenzophenone is greatly lowered, and complicated stages are required for the recovery of solvents used for the purification and for the treatment of residue.

Recently, it has been proposed a process in which the nitration of benzophenone is conducted by using a large amount of oleum to selectively nitrate the meta-position. However, this process has problems in the disposal of a large amount of waste acid and materials for the apparatus [A. Onopchenko et al., J. Org. Chem., 46, 5014(1981)].

3,4'-Dinitrobenzophenone may be prepared, for example, by a process in which 4-nitrobenzyl alcohol is reacted with nitrobenzene to obtain 3,4'-dinitrodiphenylmethane which is then oxidized with chromic acid [P.J. Montagne, Ber., 49, 2293-2294 (1916)]; a process in which diphenylacetic acid is nitrated with fuming nitric acid to obtain 3,4'-dinitrodiphenylacetic acid which is then oxidized with chromic acid [I. Moyer Hunsberger et al., J. Am. Chem. Soc., 71, 2635-2639(1949)]; and a process in which 4-nitrobenzophenone is nitrated [Vernon, Li Bell et al., J. Org. Polymer. Chem., 14, 2277(1976)].

However, these processes have disadvantages in that very complicated reactions must be conducted, large amounts of by-products such as isomers must be removed, purification by recrystallization must be repeated and the disposal of waste acid and waste metals requires much cost.

Further, the separation of the tin compound used in the reduction of the dinitrobenzophenones is troublesome. Care must be taken lest trace amounts of the metal should remain. Much cost and effort are required for the disposal of waste metal and waste acid to prevent them from causing environmental pollution.

Therefore, the conventional processes of preparing dinitrobenzophenones and reducing them to diaminobenzophenones are industrially very unfavourable from the viewpoints of economy and environmental protection. Thus an improved process for the preparation of 3,4'-diaminobenzophenone, from which disadvantages associated with the prior art are eliminated has been eagerly sought.

SUMMARY OF THE INVENTION

An object of the present invention is to provide an industrially and economically advantageous process for the preparation of 3,3'- or 3,4'-diaminobenzophenone.

Another object of the present invention is to provide a process for the preparation of 3,3'- or 3,4'-diaminobenzophenone, which does not require the troublesome separation and purification operations of intermediate compounds in the production of 3,3'- or 3,4'-diaminobenzophenone starting from 3- or 4-nitrobenzoyl chloride and chlorobenzene, gives good yields in a high purity and makes it possible to prepare the desired products inexpensively.

In accordance with the present invention, it is possible to prepare 3,3'- or 3,4'-diaminobenzophenone in a high yield and in a high purity by subjecting 3- or 4-nitrobenzoyl chloride and chlorobenzene in the presence of a Lewis acid catalyst to the Friedel-Crafts reaction, nitrating the resulting mixture of chlorobenzophenone isomers without purifying it, and catalytically reducing and dechlorinating the resulting chlorodinitrobenzophenone mixture in the presence of a reduction catalyst and a dehydrochlorinating agent.

In accordance with the present invention, the Friedel-Crafts reaction between 3- or 4-nitrobenzoyl chloride and chlorobenzene gives an isomer mixture which is then nitrated, and the resulting isomer mixture is reduced and dechlorinated to give the desired 3,3'- or 3,4'-diaminobenzophenone. Thus, the desired product can be prepared from intermediate products themselves containing various isomers formed in two stages (the Friedel-Crafts reaction and nitration reaction) during the course of the reaction starting with 3- or 4-nitrobenzoyl chloride and leading to 3,3'- or 3'4'-diaminobenzophenone. Namely, the intermediate products used in this process need not be separated from undesirable isomers to isolate the suitable product.

DETAILED DESCRIPTION OF THE INVENTION

The process of the present invention is conducted in the following manner.

(1) Nitrobenzoyl chloride and chlorobenzene are subjected to the Friedel-Crafts reaction in the presence of a Lewis acid catalyst to obtain a chloronitrobenzophenone mixture. For example, 3-nitrobenzoyl chloride is reacted with chlorobenzene in the presence of anhydrous aluminum chloride catalyst to obtain a mixture composed of 4'-chloro-3-nitrobenzophenone and 2'-chloro-3-nitrobenzophenone. Alternatively, 4-nitrobenzoyl chloride is reacted with chlorobenzene in the presence of anhydrous aluminum chloride or anhydrous ferric chloride to obtain a mixture composed of 4'-chloro-4-nitrobenzophenone and 2'-chloro-4-nitrobenzophenone. (2) When these mixtures are nitrated, a nitro group is introduced only into a metaposition with respect to the carbonyl group of the benzene ring having a chloro group. Therefore, the mixture composed of 4'-chloro-3-nitrobenzophenone and 2'-chloro-3-nitrobenzophenone gives a mixture composed of 4'-chloro-3,3'-dinitrobenzophenone, 2'-chloro-3,3'-dinitrobenzophenone and 2'-chloro-3,5'-dinitrobenzophenone. The mixture composed of 4'-chloro-4-nitrobenzophenone and 2'-chloro-4-nitrobenzophenone gives a mixture composed of 4'-chloro-3',4-dinitrobenzophenone, 2'-chloro-3',4-dinitrobenzophenone and 2'-chloro-4,5'-dinitrobenzophenone.

(3) When these mixtures are catalytically reduced and dehalogenated in the presence of a reduction catalyst and a dehydrohalogenating agent, only the corresponding 3,3'- or 3,4'-diaminobenzophenone can be obtained in a high yield industrially ad- vantageously.

In the process of the present invention, 3-or 4-nitrobenzoyl chloride and chlorobenzene are firstly subjected to the Friedel-Crafts reaction (hereinafter referred to as the first-stage reaction). In the first-stage reaction, chlorobenzene is used in an amount of 1.1 to 3 times by mol that of nitrobenzoyl chloride. Any of catalysts which can be used in the Friedel-Crafts reaction may be used. Examples of such catalysts include Lewis acids such as anhydrous aluminum chloride, anhydrous ferric chloride, anhydrous ferric sulfate and boron trifluoride. As to the amounts of these catalysts to be used, anhydrous aluminum chloride is used in an amount of 1 to 2 mol per mol of nitrobenzoyl chloride, and anhydrous ferric chloride, anhydrous sulfate and boron trifluoride are used in an amount of 0.005 to 0.1 mol, preferably 0.01 to 0.05 mol per mol of nitrobenzoyl chloride.

The reaction is conducted at a temperature of 0° to 80° C., preferably 10° to 60° C., when anhydrous aluminum chloride catalyst is used. When anhydrous ferric chloride, anhydrous ferric sulfate or boron trifluoride is used as a catalyst, the reaction is conducted at the reflux temperature of an excess of chlorobenzene, i.e., at a temperature of 140° to 180° C. until the evolution of hydrogen chloride gas ceases. The termination of the reaction can be ascertained by determining the amount of hydrogen chloride gas evolved, or by confirming the amount of the consumed nitrobenzoyl chloride by means of gas chromatography or high performance liquid chromatography.

After the completion of the reaction, an excess of chlorobenzene is distilled off under reduced pressure or by steam distillation to obtain a crude chloronitrobenzophenone mixture.

In the subsequent nitration reaction, this chloronitrobenzophenone mixture is nitrated to prepare chlorodinitrobenzophenes (hereinafter referred to as the second-stage reaction). This second-stage reaction may be conducted under the same conditions in all cases irrespective of the contents of the 2'-chloro and the 4'-chloro compounds in the chloronitrobenzophenone mixture obtained in the first stage reaction.

As the nitrating agents, mixed acid, fuming nitric acid, nitric acid/acetic acid and other conventional nitrating agents may be used. Generally, the mixed acid and fuming nitric acid are preferred.

By using these nitrating agents, the second-stage reaction is conducted in the following manner.

When the nitration is conducted with fuming nitric acid, 95% nitric acid is used in an amount of 4 to 6 mol per mol of the crude chloronitrobenzophenone. When the nitration is conducted with a mixed acid, the one comprising a combination of concentrated sulfuric acid and nitric acid or a nitrate such as sodium nitrate or potassium nitrate is used in a molar ratio of the combined amount of nitric acid or the nitrate and concentrated sulfuric acid to the chloronitrobenzophenone of 1:1.1 - 1.5:2 - 3.

If necessary, a halogenated hydrocarbon solvent such as dischloromethane, 1,2-dichloroethane, 1,1,2-trichloroethane, chloroform, carbon tetrachloride, 1,1,2,2-tetrachloroethane or trichloroethylene may be used in the nitration reaction.

The reaction is conducted by mixing the crude chloronitrobenzophenone mixture, a nitrating agent and, if necessary, a solvent. When the reaction is conducted by using a mixed acid as a nitrating agent, the crude chloronitrobenzophenone is introduced into the mixed acid which has been previously prepared. Alternatively, nitric acid or the nitrate is added to a mixture of sulfuric acid and the starting material. The chloronitrobenzophenone mixture and the mixed acid are thoroughly mixed together. Then the nitration reaction is conducted by heating the mixture with stirring. The reaction temperature is in the range of 20° to 100° C. The reaction time is in the range of 2 to 15 hours.

The termination of the reaction can be determined by means of thin-layer chromatography or high performance liquid chromatography. After the completion of the reaction, the chlorodinitrobenzophenone mixture prepared in the second-stage reaction can be recovered by any of conventional methods. For example, when a solvent is not used, the reaction mixture is diluted with water or ice water to precipitate the product which is then recovered by filtration. When a solvent is used, the reaction mixture is separated into a solvent layer and a waste acid layer, or is diluted with water. The solvent is distilled off by steam distillation. The resulting product is recovered by filtration.

As mentioned above, there can be obtained in the second-stage reaction the chlorodinitrobenzophenone where the nitro group has been introduced into a metaposition with respect to the carbonyl group of the benzene ring having a chloro group. When 3-nitrobenzoyl chloride is used as a starting material, the product is a mixture consisting of 4'-chloro-3,3'-dinitrobenzophenone, 2'-chloro-3,3'-dinitrobenzophenone and 2'-chloro-3,5'-dinitrobenzophenone. When 4-nitrobenzoyl chloride is used as a starting material, the product is a mixture consisting of 4'-chloro-3',4-dinitrobenzophenone, 2'-chloro-3',4-dinitrobenzophenone and 2'-chloro-4,5'-dinitrobenzophenone.

Without isolating each of the chlorodinitrobenzophenones, these mixtures may be subjected to the subsequent reduction and dechlorination reaction (hereinafter referred to as the thirdstage reaction) to prepare the desired 3,3'- or 3,4'-diaminobenzophenone.

The third-stage reaction can be conducted, e.g., in the following manner. In case (a), crude chlorodinitrobenzophenones are dissolved or suspended in a solvent. A reduction catalyst is added thereto. Then hydrogen is introduced into the mixture with stirring at a predetermined temperature to effect the reduction of the nitro groups followed by the addition of a dehydrochlorinating agent to effect a dechlorination reaction. In case (b), the dehydrochlorinating agent is added together with the reduction catalyst. Hydrogen is introduced into the mixture with stirring at a predetermined temperature to simultaneously conduct the reduction of the nitro groups and the dechlorination reaction. In any case the reaction proceeds smoothly to form the desired 3,3'- or 3,4'-diaminobenzophenone. However, since the chlorine atom of the starting chlorodinitrobenzophenone is nucleophilic, a side reaction between the chlorine atom and the dechlorinating agent takes place under certain conditions to lower the yield of the desired product. Thus, the method (a) is preferred.

As the reduction catalysts used in the thirdstage reaction, any of conventional metal catalysts for catalytic reduction may be used. Examples of the metals include nickel, palladium, platinum, rhodium, ruthenium, cobalt and copper. Palladium catalyst is industrially preferred. These catalysts may be used in a metallic form. Usually, these metals are supported on a catalyst carrier such as carbon, barium sulfate, silica gel or alumina. Nickel, cobalt or copper may be used in the form of a Raney catalyst.

The catalyst is used in an amount of 0.01 to 10% by weight based on that of the crude chlorodinitrobenzophenone. When the catalyst is used in the form of a metal, the amount is usually in the range of 2 to 8% by weight. When the catalyst is supported on a carrier, the amount is in the range of 0.05 to 5% by weight.

As the dehydrochlorinating agents, alkali metal or alkaline earth methal oxides, hydroxides and bicarbonates, alkali metal or alkaline earth metal salts of lower fatty acids, ammonia and organic amines may be used. Examples of such dehydrochlorinating agents are calcium carbonate, sodium hydroxide, magnesium oxide, ammonium bicarbonate, calcium oxide, lithium hydroxide, barium hydroxide, potassium carbonate, potassium hydroxide, sodium acetate, potassium propionate, ammonia, triethylamine, tri-n-butylamine, triethanolamine, pyridine, N-methylmorpholine and mixtures thereof.

The dehydrochlorinating agent is used in an amount of 0.2 to 5 times by mol, preferably 0.5 to 2 times by mol that of the crude chlorodinitrobenzophenone.

Usually, the reaction is carried out in an organic solvent. Any of organic solvents which are inert to the reaction may be used without particular limitation. Examples of such solvents include alcohols such as methanol, ethanol and isopropyl alcohol; glycols such as ethylene glycol and propylene glycol; ethers such as ehter, dioxane, tetrahydrofuran and methyl cellosolve; aliphatic hydrocarbons such as hexane and cyclohexane; esters such as ethyl acetate and butyl acetate; halogenated hydrocarbons such as dichloromethane, chloroform, carbon tetrachloride, 1,2-dichloroethane, 1,1,3trichloroethane and tetrachloroethane; dimethylformamide and dimethyl sulfoxide. When a solvent immiscible with water is used and the reaction proceeds too slow, the reaction can be accelerated by adding a conventional phase transfer catalyst such as a quaternary ammonium salt or a quaternary phosphonium salt. The solvent is used in an amount sufficient to suspend or completely dissolve the chlorodinitrobenzophenone. Usually, the solvent is used in an amount of 0.5 to 10 times by weight that of the starting material.

The reaction temperature is not critical and usually within the range of 20° to 200° C., preferably 20° to 100° C. The reaction pressure is usually within the range of from atmospheric pressure to 50 kg/cm² G.

The termination of the reaction can be confirmed by determining the amount of hydrogen consumed or by means of thin layer chromatography. After the completion of the reaction, the catalyst and inorganic salts are removed by filtering the reaction solution with heating or by extraction. If necessary, the resulting solution is concentrated to precipitate 3,3'- or 3,4'-diaminobenzophenone as a crystal. Alternatively, hydrogen chloride gas is bubbled through the reaction solution after the removal of the catalyst and the inorganic salts to isolate the product as 3,3'- or 3,4'-diaminobenzophenone hydrochloride.

The following examples further illustrate the present invention in more detail.

EXAMPLE 1

2.7 g (0.02 mol) of anhydrous ferric chloride was added to a mixture of 185.5 g (1.0 mol) of 3-nitrobenzoyl chloride and 124 g (1.1 mol) of chlorobenzene. While introducing nitrogen gas into the reactor, the reaction was conducted with stirring at a temperature of 140° to 150° C. for 19 hours. After the completion of the reaction, an excess amount of chlorobenzene was distilled at the same temperature under reduced pressure to recover it. Then the reaction mixture was cooled to 80° C. and 500 ml of 1,2-dichloroethane was added thereto to form a homogeneous solution. While keeping the temperature at 70° to 75° C., 335 g (5 mol) of 94% nitric acid (d = 1.50) was added dropwise to the above solution over a period of two hours. After the completion of the addition, the reaction was continued at the reflux temperature of 1,2-dichloroethane for 12 hours to complete the nitration reaction. 1,2-Dichloroethane was distilled off to precipitate light brown particulate chlorodinitrobenzophenone. This product was recovered by filtration, washed with water, and dried to give 286 g (over-all yield 93.2%) of crude chlorodinitrobenzophenone.

The analysis by means of high performance liquid chromatography revealed that the crude reaction product consisted of the following composition:

| | |
|---|---|
| 4'-chloro-3,3'-dinitrobenzophenone | 82.8% |
| 2'-chloro-3,3'-dinitrobenzophenone | ⎫ |
| | ⎬ 12.4% |
| 2'-chloro-3,5'-dinitrobenzophenone | ⎭ |
| other products | 5.8% |

30.7 g (0.1 mol) of this crude chlorodinitrobenzophenone, 0.31 g of 5% Pd/C (a product of Nippon Engelhardt K.K.) and 200 ml of ethanol were charged in a closed glass vessel equipped with a thermometer and a stirrer. While vigorously stirring the mixture at 45±2° C., hydrogen was introduced thereinto and 11.76 l(0.525 mol) of hydrogen was absorbed in 7 hours. The reaction mixture was cooled to 30±2° C. and 11 g of 28% aqueous ammonia was added thereto. Hydrogen was introduced at the same temperature and 3.84 l (0.17 mol) of hydrogen was absorbed in 5 hours. After the completion of the reaction, the temperature of the reaction mixture was raised to 75° to 80° C. The catalyst and contaminants were removed by filtering the reaction mixture with heating. The filtrate was cooled to precipitate 3,3'-diaminobenzophenone as a yellow crystal. The crystal was recovered by filtration, washed with a 50% aqueous ethanol solution, and dried to give 15.3 g (yield 72.2% based on the crude chlorodinitrobenzophenone) of a product with m.p. of 148° to 149.5° C. This product was recrystallized from water to give pure 3,3'-diaminobenzophenone as a light yellow needle crystal with m.p. of 149° to 150° C.

Elemental analysis: Calculated (%): C73.5, H5.7, N13.2. Found (%): C73.5, H5.8, N13.2.

EXAMPLES 2 to 4

146.6 g (1.1 mol) of anhydrous aluminum chloride was added to a mixture of 185.5 g (1.0 mol) of 3-nitrobenzoyl chloride and 225 g (2.0 mol) of chlorobenzene. The reaction was conducted at a temperature of 50° to 60° C. for 3 hours. After the completion of the reaction, the contents were poured into 2 l of ice water. The resulting organic layer was separated and subjected to steam distillation to distill off an excess amount of chlorobenzene and to precipitate greyish white particulate chloro-nitrobenzophenone. This product was recovered by filtration, washed with water, and dried to give 252.7 g (crude yield 96.6%) of crude chloro-nitrobenzophenone.

This crude chloronitrobenzophenone was dissolved in 500 ml of methylene chloride and 250 g (2.5 mol) of concentrated sulfuric acid and 93.5 g (1.1 mol) of sodium nitrate were added thereto. The mixture was reacted at a temperature of 35° to 40° C. for 7 hours. After the completion of the reaction, 500 ml of ice water was carefully added thereto. Methylene chloride was removed by heating. The precipitated light brown particulate material was recovered by filtration, washed with water, and dried to give 293 g (over-all yield 95.5%) of crude chlorodinitrobenzophenone.

The analysis by means of high performance liquid chromatography revealed that the crude reaction product consisted of the following composition:

| | |
|---|---|
| 4'-chloro-3,3'-dinitrobenzophenone | 96.7% |
| 2'-chloro-3,3'-dinitrobenzophenone | |
| 2'-chloro-3,5'-dinitrobenzophenone | } 3.1% |
| other products | 0.2% |

Then the experiment of Example 1 was repeated except that the amount of the crude chlorodinitrobenzophenone, the catalysts, the solvents, the dehydrochlorinating agents and pressures given in Table 1 were employed. The results are shown in Table 1.

EXAMPLE 5

4 g (0.03 mol) of ferric chloride was added to a mixture of 185.5 g (1.0 mol) of 4-nitrobenzoyl chloride and 135 g (1.2 mol) of chlorobenzene. While introducing nitrogen gas into the reactor, the reaction was conducted with stirring at a temperature of 140° to 155° C. After the completion of the reaction, the reaction mixture was cooled to 90° C. and 200 ml of hot water was added thereto. An excess amount of chlorobenzene was recovered by steam distillation. Then the contents were cooled and the product was recovered by filtration and dried to give 246.7 g (crude 94.3%) of brown particulate crude chloronitrobenzophenone.

This crude chloronitrobenzophenone was nitrated at a temperature of 50° to 60° C. for 3 hours by using a mixed acid consisting of 250 g (2.5 mol) of concentrated sulfuric acid and 80 g (1.2 mol) of 94% nitric acid (d = 1.50). After the completion of the reaction, the reaction mixture was cooled and poured into 2 l of ice water. The product was recovered by filtration and dried to give 283.9 g (over-all yield 92.6%) of pale brown particulate crude chlorodinitrobenzophenone.

The analysis by means of high performance liquid chromatography revealed that the crude reaction product consisted of the following com- position:

| | |
|---|---|
| 4'-chloro-3',4-dinitrobenzophenone | 86.2% |
| 2'-chloro-3',4-dinitrobenzophenone | |
| 2'-chloro-4,5'-dinitrobenzophenone | } 10.7% |
| other products | 3.1% |

Then the experiment of Example 1 was repeated in all essential details except that the amount of the crude chlorodinitrobenzophenone, the catalysts, the solvents, the dehydrochlorinating agents and pressures given in Table 1 were employed. The results are shown in Table 1.

EXAMPLE 6

The experiment of Example 5 was repeated except that 4-nitrobenzoyl chloride was used as a starting material. 294.3 g (over-all yield 96%) of crude chloronitrobenzophenone was obtained. The analysis by means of high performance liquid chromatography revealed that the crude reaction product consisted of the following composition:

| | |
|---|---|
| 4'-chloro-3',4-dinitrobenzophenone | 96.3% |
| 2'-chloro-3',4-dinitrobenzophenone | |
| 2'-chloro-4,5'-dinitrobenzophenone | } 3.4% |
| other products | 0.3% |

30.7 g (0.1 mol) of this crude chlorodinitrobenzophenone, 1 g of palladium black catalyst (a product of Nippon Engelhardt K.K.) and 100 ml of isopropyl alcohol were charged in the same reactor as that of Example 1. While vigorously stirring the mixture at a temperature of 25° to 30° C., hydrogen was introduced thereinto and 10.2 l (0.455 mol) of hydrogen was absorbed in 10 hours. Then 12.2 g (0.12 mol) of triethylamine was added and hydrogen was introduced thereinto. 5.2 l (0.232 mol) of hydrogen was absorbed in 5 hours. After the completion of the reaction, the temperature of the reaction mixture was raised to 70 to 80° C. The catalyst and contaminants were removed by filtration with heating. The filtrate was cooled to precipitate 3,4'-diaminobenzophenone as a yellow crystal. This crystal was recovered by filtration, washed with 15 ml of isopropyl alcohol, washed with water, and dried to give 17.7 g (yield 83.5%) of a product with m.p. of 126.5° C. This product was recrystallized from water to give pure 3,4'-diaminobenzophenone as a pale yellow needle crystal with m.p. of 126.3° to 127.9° C.

Elemental analysis: Calculated (%): C73.5, H5.7, N13.2. Found (%): C73.4, H5.7, N13.1.

EXAMPLE 7

30.7 g (0.1 mol) of crude chlorodinitrobenzophenone obtained in Example 6, 1.5 g to 5% Pd/C 22.2 g (0.3 mol) of calcium hydroxide, 800 ml of methylene chloride and 1 g of a 90% aqueous solution of trioctylmethylammonium chloride (a reagent of Tokyo Kasei K.K.) were charged in an autoclave. While vigorously stirring the mixture at a temperature of 35° to 40° C., hydrogen was introduced and the pressure was kept at 10 to 12 kg/cm² G. The reaction was continued for 11 hours. The catalyst and contaminants were removed by filtration. An organic layer was separated from the filtrate. Hydrogen chloride gas was bubbled through the organic layer until the layer was saturated. The precipitated crude crystal was recovered by filtration. Yield: 21.8 g (76.5%). This crystal was recrystallized from a 20% aqueous isopropyl alcohol solution to give 3,4'-diaminobenzophenone hydrochloride as a light yellowish white needle crystal with m.p. above 250° C.

Elemental analysis: Calculated (%): C54.7, H4.9, N9.8, Cl24.9. Found (%): C54.5, H5.0, N9.9, Cl24.7.

EXAMPLE 8

The experiment of Example 1 was repeated in all essential details except that the amount of. the crude chlorodinitrobenzophenone obtained in Example 6, the catalysts, the solvents, the dehydrochlorinating agents and pressure given in Table 1 were employed. The results are shown in Table 1.

nitrobenzophenone or a mixture of 4'-chloro-4-nitrobenzophenone and 2'-chloro-4-nitrobenzophenone obtained by the Friedel-Crafts reaction is directly subjected to the subsequent nitration reaction without isolating each isomeric component.

3. A process as set forth in claim 1, wherein a mixture consisting of 4'-chloro-3,3'-dinitrobenzophenone, 2'-chloro-3,3'-dinitrobenzophenone and 2'-chloro-3,5'-dinitrobenzophenone or a mixture consisting of 4'-chloro-3',4-dinitrobenzophenone, 2'-chloro-3',4-dinitrobenzophenone and 2'-chloro-4,5'-dinitrobenzophenone obtained by the nitration reaction is directly subjected to the subsequent reduction and dechlorination reactions without isolating each isomeric component.

4. A process as set forth in claim 1, wherein the third-stage reaction is carried out in such a manner that the reduction reaction is carried out in the crude chlorodinitrobenzophenone mixture by adding a reduction

TABLE 1

| Example No. | Starting material (mol) | Catalyst (g) | | Solvent (ml) | | Dehydrochlorinating agent (mol) | | Temperature (°C.) | Pressure (kg/cm².G) | Time (hr) | Desired product yield (%) |
|---|---|---|---|---|---|---|---|---|---|---|---|
| 2 | 0.1 | 5% Pt/C | 1.5 | dioxane | 100 | 20% aqueous caustic soda solution | 0.1 | 70~80 | normal pressure | 18 | 3,3'-DABP* 81.6 |
| 3 | 0.1 | Raney nickel | 3 | ethyl cellosolve | 100 | magnesium chloride | 0.08 | 95~100 | 5~7 | 10 | 3,3'-DABP 80.6 |
| 4 | 0.1 | 5% Pd/C | 0.3 | THP | 60 | sodium acetate | 0.16 | 20~30 | normal pressure | 9 | 3,3'-DABP 80.1 |
| 5 | 0.1 | 5% Pd/C | 0.6 | isopropanol | 100 | 20% aqueous ammonia | 0.12 | 30~45 | normal pressure | 15 | 3,4'-DABP 74.7 |
| 8 | 0.1 | 5% Pd—Rh/C | 0.6 | methanol | 60 | calcium carbonate | 0.1 | 30~45 | normal pressure | 18 | 3,4'-DABP 82.5 |

*Note:
DABP = diaminobenzophenone

What is claimed is:

1. A process for the preparation of 3,3'- or 3,4'-diaminobenzophenone, which comprises nitrating a chloronitrobenzophenone mixture obtained by the Friedel-Crafts reaction between 3- or 4-nitrobenzoyl chloride and chlorobenzene and then catalytically reducing and dechlorinating the resulting chlorodinitrobenzophenone mixture in the presence of a reduction catalyst and a dehydrochlorinating agent.

2. A process as set forth in claim 1, wherein a mixture of 4'-chloro-3-nitrobenzophenone and 2'-chloro-3-catalyst and by introducing hydrogen and the dechlorination reactionis carried out by adding a dehydrochlorinating agent.

5. A process as set forth in claim 1, wherein the third stage reaction is carried out in such a manner that the dehydrochlorinating agent is added together with the reduction catalyst, and hydrogen is introduced to carry out simultaneously the reduction and the dechlorination reaction.

* * * * *